US012616921B2

(12) United States Patent
Choi et al.

(10) Patent No.: US 12,616,921 B2
(45) Date of Patent: May 5, 2026

(54) PROCESS FOR THE DEPROTECTION OF OLIGONUCLEOTIDES

(71) Applicant: Hoffmann-La Roche Inc., Little Falls, NJ (US)

(72) Inventors: Yong Rag Choi, Seoul (KR); Younggoo Kang, Seoul (KR); Sung Won Kim, Seoul (KR); Kyeong Eun Jung, Seoul (KR); Pascal Schmidt, Eimeldingen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 730 days.

(21) Appl. No.: 17/570,225

(22) Filed: Jan. 6, 2022

(65) Prior Publication Data

US 2022/0410035 A1 Dec. 29, 2022

Related U.S. Application Data

(63) Continuation of application No. PCT/EP2020/068922, filed on Jul. 6, 2020.

(30) Foreign Application Priority Data

Jul. 9, 2019 (EP) ..................................... 19185225

(51) Int. Cl.
| | |
|---|---|
| B01D 15/36 | (2006.01) |
| B01D 15/20 | (2006.01) |
| C07H 21/02 | (2006.01) |
| C07H 21/04 | (2006.01) |

(52) U.S. Cl.
CPC ........... B01D 15/363 (2013.01); C07H 21/02 (2013.01); C07H 21/04 (2013.01); B01D 15/203 (2013.01)

(58) Field of Classification Search
CPC .............................. B01D 15/363; C07H 21/00
See application file for complete search history.

(56) References Cited

U.S. PATENT DOCUMENTS

| | | |
|---|---|---|
| 2004/0048251 A1 | 3/2004 | Vargeese |
| 2004/0185491 A1 | 9/2004 | Krotz et al. |
| 2005/0136458 A1 | 6/2005 | Dale et al. |

FOREIGN PATENT DOCUMENTS

| | | |
|---|---|---|
| WO | 2003/080834 | 10/2003 |
| WO | 2004/020449 | 3/2004 |
| WO | 2006/076674 | 7/2006 |
| WO | 2007/063940 A1 | 6/2007 |
| WO | 2007/066567 A1 | 6/2007 |
| WO | 2019/023439 A1 | 1/2016 |
| WO | 2019/105418 A1 | 6/2019 |
| WO | 2020/191252 | 9/2020 |

OTHER PUBLICATIONS

Shaikh, May 2019, IEX Purification of RNA Base(s) Containing DMT-on Oligonucleotide Single Strand Using a One Step On-Column Detritylation Technique, Master's thesis, Harvard Extension School. (Year: 2019).*
Schulhof, Nucleic Acids Research, vol. 15, No. 2, 1987. (Year: 1987).*
Shanagar, J. Biochem. Biophys. Methods 64 (2005) 216-225. (Year: 2005).*
Paredes, E., Konishi, T. (2018). Large-Scale Oligonucleotide Manufacturing. In: Obika, S., Sekine, M. (eds) Synthesis of Therapeutic Oligonucleotides. Springer, Singapore. (Year: 2018).*
"International Preliminary Report on Patentability—PCT/EP2020/068922" (Report Issuance Date: Jan. 11, 2022; Chapter I),:pp. 1-7 (Jan. 20, 2022).
"International Search Report—PCT/EP2020/068922" (w/Written Opinion), :pp. 1-9 (Sep. 8, 2020).
Zhang et al., "Practical Experimental Techniques in Cellular and Molecular Immunology" Fourth Military Medical University Press: 174-175 (Apr. 30, 2013) w/English Machine Translation.

* cited by examiner

*Primary Examiner* — Layla D Berry

(57) ABSTRACT

The invention relates to a new process for the purification of oligonucleotides which comprises the removal of an acid labile 5'hydroxy protecting group at the 5'-O-oligonucleotide terminus of the oligonucleotide by means of an on-column de-protection with an acid.

14 Claims, No Drawings

Specification includes a Sequence Listing.

PROCESS FOR THE DEPROTECTION OF OLIGONUCLEOTIDES

CROSS REFERENCE TO RELATED APPLICATIONS

This application is a continuation of International Application No. PCT/EP2020/068922, filed Jul. 6, 2020, which claims priority to European Patent Application No. 19185225.0, filed Jul. 9, 2019, which are incorporated herein by reference in its entirety.

SEQUENCE LISTING

This application contains a Sequence Listing, which has been submitted electronically in ASCII format and is hereby incorporated by reference in its entirety. Said ASCII copy, created on Jun. 21, 2022, is named P35629-US-SL.txt and is 655 bytes in size.

The invention relates to a new process for the purification of oligonucleotides which comprises the removal of an acid labile 5'hydroxy protecting group at the 5'-O -oligonucleotide terminus of the oligonucleotide by way of an on-column de-protection with an acid.

The oligonucleotide which is typically prepared via solid phase synthesis, after its cleavage from the solid support, still contains a significant amount of impurities. For standard monomers of a 15- to 20-mer length the API purity is at best in the range of 70 to 80%. For chemically modified monomers or for longer sequences the API content is typically even lower.

Selective separation methods have been developed to prepare high purity oligonucleotides which satisfy the specifications for a therapeutic application.

In one method the oligonucleotide, after its cleavage from the solid support, is left with the acid labile 5'hydroxy protecting group at the 5'-O-oligonucleotide terminus. The hydrophobicity of this group allows the application of effective chromatography techniques for purification.

It is common strategy that the crude oligonucleotide is passing the following steps (for instance Krotz et al, Organic Process Research & Development 2003, 7, 47-52):
a) reversed phase chromatography
b) concentration and desalting
c) removal of the acid labile 5'hydroxy protecting group in solution and d) further concentration and desalting It was found that this known processes require substantial operation time due to the number of single operation steps a) to d).

Object of the invention was to reduce the number of purification steps and with that reduce the operation time and also attempt to reach a higher overall yield.

It was found that the object of the invention could be reached with the novel process for the purification of oligonucleotides as outlined above.

The following definitions are set forth to illustrate and define the meaning and scope of the various terms used to describe the invention herein.

The term acid labile 5'hydroxy protecting group is defined as a protecting group which is cleavable with the help of a suitable acid and which has a hydrophobic character.

Typical acid labile 5'hydroxy protecting groups are selected from 4,4'-dimethoxytrityl, 4-methoxytrityl, trityl, 9-phenyl-xanthen-9-, 9-(p-tolyl)-xanthen-9-yl or from tert-butyldimethylsilyl, preferably from 4,4'-dimethoxytrityl, 4-methoxytrityl or trityl or even more preferably from 4,4'-dimethoxytrityl.

The term oligonucleotide as used herein is defined as it is generally understood by the skilled person as a molecule comprising two or more covalently linked nucleotides. For use as a therapeutically valuable oligonucleotide, oligonucleotides are typically synthesized containing 10 to 40 nucleotides, preferably 10 to 25 nucleotides in length.

The oligonucleotides may consist of optionally modified DNA, RNA or LNA nucleoside monomers or combinations thereof.

The LNA nucleoside monomers are modified nucleosides which comprise a linker group or a bridge between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, RNA or LNA nucleoside by the introduction of one or more modifications of the sugar moiety or the nucleobase moiety. In a preferred embodiment the modified nucleoside comprises a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleosides are as a rule linked by a phosphodiester (P=O) and/or a phosphorothioate (P=S) internucleoside linkage which covalently couples two nucleosides together.

Accordingly, in some oligonucleotides all internucleoside linkages may consist of a phosphodiester (P=O), in other oligonucleotides all internucleoside linkages may consist of a phosphorothioate (P=S) or in still other oligonucleotides the sequence of internucleoside linkages vary and comprise both phosphodiester (P=O) and phosphorothioate (P=S) internucleoside linkages.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}C$ (5-methyl cytosine) for DNA nucleosides. Modified nucleobases include but are not limited to nucleobases carrying protecting groups such as tert-butylphenoxyacetyl, phenoxyacetyl, benzoyl, acetyl, isobutyryl or dimethylformamidino (see Wikipedia, Phosphoramidit-Synthese, https://de.wikipedia.org/wiki/Phosphoramidit-Synthese of Mar. 24, 2016).

The principles of the oligonucleotide synthesis are well known in the art (see e.g. Oligonucleotide synthesis; Wikipedia, the free encyclopedia; https://en.wikipedia.org/wiki/Oligonucleotide synthesis, of Mar. 15, 2016).

Larger scale oligonucleotide synthesis nowadays is carried out automatically using computer controlled synthesizers.

As a rule, oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from Cytiva or the NittoPhase®HL support from Kinovate.

The oligonucleotide synthesis in principle is a stepwise addition of nucleotide residues to the 5'-terminus of the growing chain until the desired sequence is assembled.

As a rule, each addition is referred to as a synthetic cycle and in principle consists of the chemical reactions $a_1$) de-blocking the 5'protected hydroxyl group on the solid support, $a_2$) coupling the first nucleoside as activated phosphoramidite with the free 5'hydroxyl group on the solid support, $a_3$) oxidizing or sulfurizing the respective P-linked nucleoside to form the respective phosphodiester (P=O) or the respective phosphorothioate (P=S);

$a_4$) optionally, capping any unreacted 5'hydroxyl groups on the solid support, as) de-blocking the 5'hydroxyl group of the first nucleoside attached to the solid support;

$a_6$) coupling the second nucleoside as activated phosphoramidite to form the respective P—O linked dimer;

$a_7$) oxidizing or sulfurizing the respective P—O linked dinucleoside to form the respective phosphodiester (P=O) or the respective phosphorothioate (P=S);

$a_8$) optionally, capping any unreacted 5'hydroxyl groups;

$a_9$) repeating the previous steps as to $a_8$ until the desired sequence is assembled.

The subsequent cleavage from the solid support can be performed with concentrated aqueous ammonia. The protecting groups on the phosphate and on the nucleotide bases are also removed within this cleavage procedure.

The crude oligonucleotide after the cleavage is left with the acid labile 5'hydroxy protecting group at the 5'-O-oligonucleotide terminus.

The process for the purification of oligonucleotides comprises the removal of an acid labile 5'hydroxy protecting group at the 5'-O-oligonucleotide terminus of the oligonucleotide by way of an on-column de-protection with an acid.

The term "on column de-protection" in the context of the present invention means that deprotection of the acid labile 5'hydroxy protecting group at the 5'-O-oligonucleotide terminus takes place directly on a chromatography column, preferably on an ion—exchange chromatography column, more preferably on an anion—exchange chromatography column.

The anion-exchange chromatography is based on the competitive interaction of charged ions of the sample solution with the buffer medium employed. It can be carried out with conventional, commercially available anion-exchange resins, preferably those with trimethylammonium-functionalization. These phase materials can be obtained for example from Cytiva, Tosoh Bioscience, Bio-Rad or from Merck. Typical anion-exchange resins are the TSKgel Super Q-5PW (QAE), available from Tosoh Bioscience or the Source 30Q resin from Cytiva.

As outlined above the acid labile 5'hydroxy protecting group is typically selected from 4,4'-dimethoxytrityl, 4-methoxytrityl, trityl, 9-phenyl-xanthen-9-, 9-(p-tolyl)-xanthen-9-yl or from tert-butyldimethylsilyl, but preferably is 4,4'-dimethoxytrityl.

The on column de-protection process expediently comprises the steps a. a first equilibration of the anion-exchange column with a buffer solution comprising a phosphate salt and an organic solvent;

b. the charging of a diluted aqueous ammonia solution of the crude oligonucleotide onto the anion-exchange column c. a second equilibration of the anion-exchange column with a buffer solution comprising a phosphate salt and an organic solvent;

d. a washing of the column with a buffer solution comprising a phosphate salt, an organic solvent and alkali halide;

e. a third equilibration of the anion-exchange column with a buffer solution comprising a phosphate salt and an organic solvent;

f. the on-column de-protection with an acid;

g. a fourth equilibration of the anion-exchange column with a buffer solution comprising a phosphate salt and an organic solvent;

h. the elution of the de-protected oligonucleotide with a buffer solution comprising a phosphate salt, an organic solvent and alkali halide and a subsequent isocratic washing of the anion-exchange column with a buffer solution comprising a phosphate salt, an organic solvent and alkali halide.

The buffer solution is as a rule a phosphate buffer solution which further comprises an organic solvent and, depending on the process step, an alkali halide.

The phosphate in the buffer solution is as a rule an alkali phosphate such as a mono- or di-sodium or -potassium phosphate or mixtures thereof, but preferably is mono-sodium phosphate or a di-sodium phosphate or mixtures thereof.

The phosphate content in the buffer solution is selected between 10 mM and 40 mM, preferably between 20 mM and 30 mM.

The pH range of the buffer solution is ideally adjusted between 6.0 to 7.5.

The temperature of the buffer solution is usually maintained between 15° C. and 50° C., preferably is room temperature, i.e. between 20° C. and 40° C.

In order to prepare the diluted charging solution, the aqueous ammonia solution, which is directly obtained from the oligonucleotide synthesis, is as a rule first diluted with 1.5 to 2.5 volume eq., preferably with 2.0 volume eq. of water to achieve a dilution grade of 2.5 to 3.5, preferably of 3.0.

The diluted aqueous ammonia solution which is charged on the anion exchange column typically has a total oligonucleotide content of 8 to 20 g per L column volume, preferably 10 to 15 g per L column volume.

The organic solvent in the buffer solution can be selected from a polar protic or a polar aprotic solvent, preferably from a polar aprotic solvent more preferably from acetonitrile.

Suitable polar protic solvents are the primary aliphatic alcohols such as methanol, ethanol or i-propanol, preferably ethanol.

Suitable polar aprotic solvents are acetonitrile, dimethylsulfoxide or N-methyl-2-pyrrolidone, but preferably acetonitrile.

In a more preferred embodiment acetonitrile is used.

As a rule the buffer solution contains the organic solvent in an amount of 5 to 15% by weight, even more preferably of about 10% by weight.

For the de-protection an acid, preferably a protic acid is used.

The term protic acid shall mean an inorganic acid or an organic acid, preferably an inorganic acid or an organic acid in aqueous form and selected from hydrochloric acid, sulfuric acid, phosphoric acid, nitric acid, formic acid, or acetic acid, more preferably from acetic acid.

In a preferred embodiment the protic acid is an aqueous acetic acid with a concentration acetic acid in water of 50 to 95% by weight, more preferably of 70 to 90% by weight, even more preferably of 75% to 85% by weight.

In the washing step and the elution step the buffer solution additionally contains an alkali halide such as a sodium or potassium chloride, preferably sodium chloride.

In the washing step d) the buffer solution as a rule comprises 0.2 M to 1.0 M, preferably 0.4 M to 0.7 M of the alkali halide.

In the elution step h) and in the subsequent isocratic washing step the buffer solution typically comprises 1.5 M to 3.0 M, preferably 1.8 M to 2.5 M of the alkali halide.

The flow rate of the buffer solutions or of the acid solution is an important parameter to adjust the exposure of the buffer to the solid support-bound oligo.

As a rule the flow rate of the acid solution for the on-column deprotection is lowered compared to the flow rate for the buffers in the other steps in order to allow adjustment to the higher viscosity of the acid solution and relatively higher exposure of the acid to the acid labile 5'hydroxy protecting group.

Typically the flow rate of the acid solution in the on-column deprotection step f) is 1.5 L/min to 2.5 L/min, preferably between 1.8 L/min to 2.2 L/min.

For the other steps the flow rate of the buffer is selected in a range between 2.0 L/min to 3.0 L/min, preferably between 2.3 L/min and 2.7 L/min.

The on-column deprotection step f) and the elution step h) as a rule require relatively high amounts of the respective acid or buffer solution which is typically 10 to 30 times the column volume (CV), preferably 15 to 25 of the column volume (CV).

The oligo elution is suitably measured by UV detection and the oligo containing eluent is fractioned accordingly.

In a preferred embodiment the process further comprises the following steps, which come after the purification steps a) to h)

i) a desalting and concentration step comprising the washing of the filtrate with purified water via tangential flow filtration; and j) a lyophilization of the filtrate obtained from the desalting and concentrating step.

The tangential flow filtration is characterized in that the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate.

Suitable membranes are commercially available, for instance from Merck Millipore under the trade name Pellicon™ or from Sartorius under the tradename Hydrosart™.

The lyophilization is a technique known to the skilled person in the art and therefore can be applied accordingly.

By way of illustration of the process of the present invention the oligonucleotide of the sequence below has been selected:

(SEQ ID NO: 1)

5'-$^{Me}C_S$$^{Me}U_O$$^{Me}C_O$$\underline{A}_O$$\underline{G}_S$$T_S$$A_S$$A_S$$^{Me}C_S$$A_S$$T_S$$S_S$$T_S$$G_S$$A_S$$^{Me}C_S$$\underline{A}_O$$^{Me}$
$\underline{C}_O$$^{Me}\underline{C}_O$$A_S$$^{Me}\underline{C}$-3' 19 Na wherein"s" stands for phosphorthioate bridges, for phosphate bridges; A, G, T, U are DNA nucleoside monomers, "$^{Me}$" stands for methyl and underlined nucleosides are 2'-MOE nucleosides.

6

The compound disclosed herein has the following nucleobase sequences

SEQ ID No. 1: cucagtaacattgacaccac'

EXAMPLES

Abbreviations:

Ac$_2$O=acetic acid anhydride
(d)A=(deoxy) adenosine
(d)C=(deoxy) cytidine
(d)G=(deoxy) guanosine
DCA=dichloroacetic acid
DCI=4,5-dicyanoimidazole
DMT=4,4'-dimethoxytrityl
CV=column volume
Et$_3$N=triethylamine
EtOH=ethanol
MeCN=acetonitrile
MOE=2-methoxyethyl
NA=not applicable
NaOAc=sodium acetate
NMI=N-methyl imidazole
PADS=phenylacetyldisulfide
PhMe=Toluene
T=thymidine
U=uridine
underlined nucleosides are 2'-MOE nucleosides

Example 1 a) Synthesis of (SEQ ID NO: 1)

5'-DMT-$^{Me}C_S$$^{Me}U_O$$^{Me}C_O$$\underline{A}_O$$\underline{G}_S$$T_S$$A_S$$A_S$$^{Me}C_S$$A_S$$T_S$$T_S$$G_S$$A_S$$^{Me}C_S$
$\underline{A}_O$$^{Me}\underline{C}_O$$^{Me}\underline{C}_O$$\underline{A}_S$$^{Me}\underline{C}$-3' 19 NH$_3$ The title compound was synthesized as "DMT-on" using an ÄKTA oligopilot-100 on a 72 mmol scale.

The following phosphoramidites have been used in each cycle:

| Cycle | P-amidite |
|-------|-----------|
| 1 | MOE$^{Me}$C $^{(Bz)}$ |
| 2 | MOEA $^{(Bz)}$ |
| 3 | MOE$^{Me}$C $^{(Bz)}$ |
| 4 | MOE$^{Me}$C $^{(Bz)}$ |
| 5 | MOEA $^{(Bz)}$ |
| 6 | $^{Me}$dC $^{(Bz)}$ |
| 7 | dA $^{(Bz)}$ |
| 8 | dG (tBu) |
| 9 | T |
| 10 | T |
| 11 | dA $^{(Bz)}$ |
| 12 | $^{Me}$dC $^{(Bz)}$ |
| 13 | dA $^{(Bz)}$ |
| 14 | dA $^{(Bz)}$ |
| 15 | T |
| 16 | MOE-G $^{(iBu)}$ |
| 17 | MOEA $^{(Bz)}$ |
| 18 | MOE$^{Me}$C $^{(Bz)}$ |
| 19 | MOE$^{Me}$U |
| 20 | MOE$^{Me}$C $^{(Bz)}$ |

Synthesis parameters Cycles 3-5, 17-19

| | |
|---|---|
| Detritylation | DCA in PhMe, then MeCN |
| Coupling | Phosphoramidite (in MeCN), DCI and NMI (in MeCN), recycling loop, then MeCN |
| Oxidation | $I_2$ (in pyridine/$H_2O$), then MeCN |
| Capping | $Ac_2O$ (in MeCN), NMI (in pyridine), then PhMe |

Synthesis parameters Cycles 1-2, 6-16:

| | |
|---|---|
| Detritylation | DCA in PhMe, then MeCN |
| Coupling | Phosphoramidite (in MeCN), DCI and NMI (in MeCN), recycling loop, then MeCN |
| Sulfurization | PADS (in 3-picoline/MeCN), then MeCN |
| Capping. | $Ac_2O$ (in MeCN), NMI (in pyridine), recycling loop (only cycle 1), then PhMe |

Synthesis parameters Cycle 20:

| | |
|---|---|
| Detritylation. | DCA in PhMe, then MeCN |
| Coupling | Phosphoramidite (in MeCN), DCI and NMI (in MeCN), recycling loop, then MeCN |
| Sulfurization | PADS (in 3-picoline/MeCN), then MeCN |

| | |
|---|---|
| Backbone deprotection and cleavage/ deprotection: | a) $Et_3N$ (in MeCN), recycling loop, then PhMe<br>b) aq. $NH_4OH$, 55° C.; filtration; $H_2O$ wash | b) On-column detritylation and formation of (SEQ ID NO: 1)

5'-$^{Me}\underline{C}_S{}^{Me}\underline{U}_O{}^{Me}\underline{C}_O\underline{A}_O\underline{G}_S T_S A_S A_S{}^{Me}\underline{C}_S A_S T_S{}_S T_S \underline{G}_S A_S{}^{Me}\underline{C}_S\underline{A}_O{}^{Me}$ $\underline{C}_O{}^{Me}\underline{C}_O\underline{A}_S{}^{Me}\underline{C}$-3' 19 Na A solution of the crude material (338.87 g) obtained from example 1a) was subjected to the purification step which consists of several equilibration steps, a column wash step, an on-column detritylation step and a final product elution step.

First, the crude product from solid phase organic synthesis was loaded onto the pre-equilibrated AEX column, followed by a re-equilibration. DMT-on shortmers, capped failure sequences and other small molecules were removed by washing the column with a buffer containing a low concentration of sodium chloride. After column equilibration, the DMT group of the bound oligonucleotide was removed by aqueous acetic acid (referred to as on-column detritylation) followed by another column equilibration to remove residual acid and to establish the starting conditions of the elution step. In the last step, the product was eluted applying a high concentration sodium chloride gradient. The elution profile was monitored by ultraviolet (UV) absorption spectroscopy. The full-length DMT-off product peak was collected in several fractions. The fractions were tested for purity, organic impurities and pooled accordingly. The purification parameters are outlined in the table below:

| Parameter | Conditions |
|---|---|
| Stationary Phase | Monosized, rigid polystyrene/divinyl benzene polymer, 30 μm, Source 30Q, Cytiva |
| Column Volume (CV) | 30.0 L |
| Eluent A | 25 mM sodium phosphate[1], 10% MeCN |
| Eluent B | 25 mM sodium phosphate[1], 10% MeCN, 2M NaCl |
| Eluent C | 80% acetic acid $_{(aq)}$ |
| Eluent D | 25 mM sodium phosphate[1], 10% MeCN, 0.5M NaCl |
| Flow Rate (detritylation) | 2.0 L/min |
| Flow Rate (other steps) | 2.5 L/min |
| Temperature (gradient elution) | 37° C. |
| UV Detection Wavelength | 260 nm |
| Loading Solution from oligonucleotide synthesis | 10 L (total oligonucleotide content 32 mg/g solution) |

| Gradient | Step | % A | % B | % C | % D | CV |
|---|---|---|---|---|---|---|
| | Equilibration 1[2] | 100 | 0 | 0 | 0 | 2 |
| | Equilibration 2 | 100 | 0 | 0 | 0 | 2 |
| | Wash | 100 | 0 | 0 | 0 | 3 |
| | | 0 | 0 | 0 | 100 | |
| | | 0 | 0 | 0 | 100 | 5 |
| | Equilibration 3 | 100 | 0 | 0 | 0 | 2 |
| | Detritylation | 0 | 0 | 100 | 0 | 20 |
| | Equilibration 4 | 100 | 0 | 0 | 0 | 5 |
| | Gradient Elution | 100 | 0 | 0 | 0 | 20 |
| | | 0 | 100 | 0 | 0 | |
| | Isocratic Wash | 0 | 100 | 0 | 0 | 2 |

[1]mixture of sodium mono- and di-phosphate)
[2]Prior to loading the crude oligonucleotide solution.

c) Tangential flow Filtration/Lyophylization

Two purification batches (example 1b) were combined for the tangential flow filtration/lyophilization step.

The combined solutions (541.76 g, purity 89.2%) were concentrated and afterwards desalted by tangential flow filtration with purified water. The end of desalting was detected by conductivity of the removed permeate. The desalted solution was concentrated again and the concentration of the oligonucleotide in solution was adjusted by addition of purified water to 60-100 mg/mL. The solution was filtered through a 0.2 μm filter (Sartopore-2, Sartorius) and then lyophilized. The conditions of the performed lyophilization cycle is depicted in the table below:

| Step | Freezing | Primary Drying Sequence | | | Secondary Drying Sequence | |
|---|---|---|---|---|---|---|
| Temp (° C.) | −45 | −20 | −20 | 0 | 20 | 25 |
| Vacuum (bar) | NA | | 0.27 | | | 0.01 |

The solution obtained after rinsing was lyophilized to obtain 508.26 g of the title product purity 90.9%).

Example 2 Comparison Example a) Synthesis of (SEQ ID NO: 1)

$5\text{'-DMT-}^{Me}C_S{}^{Me}U_O{}^{Me}C_O A_O G_S T_S A_S A_S{}^{Me}C_S A_S T_S T_S G_S A_S{}^{Me}C_S \underline{A}_O{}^{Me}\underline{C}_O{}^{Me}\underline{C}_O\underline{A}_S{}^{Me}\underline{C}\text{-3'}$ 19 NH$_3$ The title compound has been prepared in accordance to example 1a.

b) HPLC

A portion of crude material was purified by HPLC (column with Amberchrom XT20 resin) according to the parameters in the Table below:

| | Step | | |
|---|---|---|---|
| | Mobile Phase A[1] (%) | Mobile Phase B[2] (%) | Column Volume (CV) |
| Gradient | 90 | 10 | 2 |
| | 60 | 40 | 20 |
| | 10 | 90 | 2 |

[1] 50 mM triethylammonium acetate (TEAA) pH 6.5-7.5

[2] Acetonitrile

The purified solution showed 97.2% purity and 90.8% yield.

c) Detritylation in solution

The pH of the combined fractions from example 2b was adjusted to pH 3 using glacial acetic acid as the detritylation agent followed by re-adjusting the pH to 5 with 10 M NaOH. The title compound was precipitated by adding the pH adjusted solution to ethanol. The yield obtained was 66.0%.

---

The invention claimed is:

1. A method for purifying oligonucleotides comprising removing an acid labile 5'hydroxy protecting group at the 5'-O-oligonucleotide terminus of the oligonucleotide by way of an on-column de-protection with acetic acid, comprising the steps:

a. passing a buffer solution comprising a phosphate salt and a polar aprotic solvent to an anion-exchange column as a first equilibration step;

b. charging a diluted aqueous ammonia solution of a crude oligonucleotide onto the column;

c. passing a buffer solution comprising a phosphate salt and a polar aprotic solvent to the column as a second equilibration step;

d. washing the column with a buffer solution comprising a phosphate salt, a polar aprotic solvent and an alkali halide;

e. passing a buffer solution comprising a phosphate salt and a polar aprotic solvent to the column as a third equilibration step;

f. passing an acid solution to the column to remove an acid labile 5'hydroxy protecting group at the 5'-O-oligonucleotide terminus of the oligonucleotide;

g. passing a buffer solution comprising a phosphate salt and a polar aprotic solvent to the column as a fourth equilibration step;

h. eluting the de-protected oligonucleotide with a buffer solution comprising a phosphate salt, a polar aprotic solvent and an alkali halide.

2. The method of claim 1, wherein the acid labile 5'hydroxy protecting group is 4,4'-dimethoxytrityl, 4-methoxytrityl, trityl, 9-phenyl-xanthen-9-, 9-(p-tolyl)-xanthen-9-yl or tert-butyldimethylsilyl.

3. The method of claim 1, wherein the phosphate salt in the at least one buffer solution is an alkali phosphate or mixtures thereof, mono sodium phosphate or di sodium phosphate or mixtures thereof.

4. The method of claim 1, wherein the phosphate salt content in at least one buffer solution is selected between 10 mM and 40 mM, or between 20 mM and 30 mM.

5. The method of claim 1, wherein the aqueous ammonia solution, which is charged on the column has a total oligonucleotide content of 8 to 20 g per L column volume, or 10 to 15 g per L column volume.

6. The method of claim 1, wherein the polar aprotic solvent in at least one buffer solution is acetonitrile.

7. The method of claim 1, wherein the alkali halide is sodium chloride.

8. The method of claim 1, wherein the buffer solution in washing step d) comprises 0.2 M to 1.0 M, or 0.4 M to 0.7 M sodium chloride.

9. The method of claim 1, wherein the buffer solution in elution step h) comprises 1.5.M to 3.0 M, or 1.8 M to 2.5 M sodium chloride.

10. The method of claim 1, wherein the flow rate of the acetic acid in step f) is between 1.5 L/min and 2.5 L/min.

11. The method of claim 1, wherein the flow rate of the buffer solution in steps a) to e) and g) to h) is between 2.0 L/min and 3.0 L/min.

12. The method of claim 1, wherein the method further comprising i. washing the filtrate from step h) with purified water via tangential flow filtration as a desalting and concentration step; and j. lyophilizing the filtrate obtained from the desalting and concentrating step i).

13. The method of claim 1, wherein the oligonucleotide consists of modified DNA, RNA or LNA nucleoside monomers or combinations thereof and is 10 to 40, or 10 to 25 nucleotides in length.

14. The method of claim 1, wherein the acetic acid is an aqueous acetic acid with a concentration of acetic acid in water of 50 to 95% by weight, 70 to 90% by weight, or 75 to 85% by weight.

\* \* \* \* \*

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
cucagtaaca ttgacaccac                                                    20